US010265493B2

(12) United States Patent
Heatherington et al.

(10) Patent No.: US 10,265,493 B2
(45) Date of Patent: Apr. 23, 2019

(54) RESPIRATORY ASSEMBLY

(71) Applicant: Stuart Heatherington, Pittsboro, NC (US)

(72) Inventors: Stuart Heatherington, Pittsboro, NC (US); Stanley S. Coe, Raleigh, NC (US)

(73) Assignee: SNAP CPAP, LLC, Pittsboro, NC (US)

( * ) Notice: Subject to any disclaimer, the term of this patent is extended or adjusted under 35 U.S.C. 154(b) by 840 days.

(21) Appl. No.: 14/876,099

(22) Filed: Oct. 6, 2015

(65) Prior Publication Data

US 2016/0022947 A1    Jan. 28, 2016

Related U.S. Application Data

(63) Continuation-in-part of application No. 13/672,946, filed on Nov. 9, 2012, now Pat. No. 9,149,595.
(Continued)

(51) Int. Cl.
*A61M 16/08* (2006.01)
*A61M 16/06* (2006.01)
(Continued)

(52) U.S. Cl.
CPC ......... *A61M 16/0825* (2014.02); *A61B 5/082* (2013.01); *A61B 5/097* (2013.01); *A61M 16/0493* (2014.02); *A61M 16/0666* (2013.01); *A61M 16/0688* (2014.02); *A61M 16/0816* (2013.01); *A61M 16/0875* (2013.01); *A61M 2016/0661* (2013.01)

(58) Field of Classification Search
CPC .......... A61M 16/0825; A61M 16/0688; A61M 16/0816; A61M 16/0875

USPC .................................................... 128/206.18
See application file for complete search history.

(56) References Cited

U.S. PATENT DOCUMENTS 2,677,371 A    5/1954  Serra
4,782,832 A   11/1988  Trimble et al.
(Continued)

FOREIGN PATENT DOCUMENTS

DE    102006016125 A1 * 10/2007  ............ A61M 16/06
EP        0821978 A2 *  2/1998  ........ A61M 16/0666
(Continued)

OTHER PUBLICATIONS

PCT, International Search Report for International Application No. PCT/US2016/055834 dated Jan. 25, 2017.
(Continued)

*Primary Examiner* — Gregory A Anderson
*Assistant Examiner* — Margaret M Luarca
(74) *Attorney, Agent, or Firm* — NK Patent Law

(57) ABSTRACT

A respiratory assembly is provided. The assembly includes at least one post having a nasal engaging portion on about a first end thereof for delivering treatment gases to the nasal cavity of a patient. A pair of tubes capable of receiving gas from a hose or fluid source are selectively engaged with the pair of posts for delivering treatment gases from the inlet through the receptacle and into the nasal cavity of the patient. A splitter may be positioned between the hose or fluid source and the pair of tubes. Ball and socket joints may provide enhanced flexibility of the assembly while in use.

21 Claims, 5 Drawing Sheets

Related U.S. Application Data

(60) Provisional application No. 61/562,056, filed on Nov. 21, 2011.

(51) Int. Cl.
*A61B 5/08* (2006.01)
*A61B 5/097* (2006.01)
*A61M 16/04* (2006.01)

(56) References Cited

U.S. PATENT DOCUMENTS

| | | | |
|---|---|---|---|
| 4,915,105 A | 4/1990 | Lee | |
| 5,513,634 A * | 5/1996 | Jackson | A61M 16/0666 128/200.26 |
| 5,676,133 A | 10/1997 | Hickle et al. | |
| 5,806,898 A | 9/1998 | Hollnagle | |
| 6,571,798 B1 * | 6/2003 | Thornton | A61M 16/06 128/206.21 |
| 7,506,649 B2 | 3/2009 | Doshi et al. | |
| 8,061,357 B2 | 11/2011 | Pierce et al. | |
| 8,215,308 B2 | 7/2012 | Doshi et al. | |
| 8,291,906 B2 | 10/2012 | Kooij et al. | |
| 2003/0094178 A1 * | 5/2003 | McAuley | A61M 16/0666 128/207.18 |
| 2004/0216747 A1 | 11/2004 | Jones, Jr. et al. | |
| 2005/0016544 A1 * | 1/2005 | Thornton | A61M 16/06 128/207.18 |
| 2006/0042631 A1 | 3/2006 | Martin et al. | |
| 2006/0124131 A1 | 6/2006 | Chandran et al. | |
| 2006/0283461 A1 | 12/2006 | Lubke et al. | |
| 2007/0163600 A1 * | 7/2007 | Hoffman | A61M 16/06 128/207.18 |
| 2008/0041373 A1 | 2/2008 | Doshi et al. | |
| 2008/0223375 A1 | 9/2008 | Cortez et al. | |
| 2009/0032026 A1 | 2/2009 | Price et al. | |
| 2009/0101147 A1 | 4/2009 | Landis et al. | |
| 2009/0194109 A1 | 8/2009 | Doshi et al. | |
| 2009/0241961 A1 | 10/2009 | McAuley et al. | |
| 2010/0229872 A1 | 9/2010 | Ho | |
| 2010/0282263 A1 | 11/2010 | Asada et al. | |
| 2011/0056497 A1 | 3/2011 | Scheiner et al. | |
| 2011/0067704 A1 | 3/2011 | Kooij et al. | |
| 2013/0131534 A1 | 5/2013 | Heatherington et al. | |
| 2014/0150798 A1 | 6/2014 | Fong et al. | |

FOREIGN PATENT DOCUMENTS

| | | |
|---|---|---|
| WO | 2008100860 A2 | 8/2008 |
| WO | 2009117163 A1 | 9/2009 |
| WO | 2014092703 A1 | 6/2014 |
| WO | 2017062677 A1 | 4/2017 |

OTHER PUBLICATIONS

PCT, Written Opinion for International Application No. PCT/US2016/055834 dated Jan. 25, 2017.

ISA/KR, PCT International Search Report for PCT/US2018/049109, dated Dec. 28, 2018.

ISA/KR, PCT Written Opinion for PCT/US2018/049109, dated Dec. 28, 2018.

* cited by examiner

RESPIRATORY ASSEMBLY

CROSS-REFERENCE TO RELATED APPLICATIONS

This application is a continuation-in-part of U.S. patent application Ser. No. 13/672,946 filed Nov. 9, 2012 and issued as U.S. Pat. No. 9,149,595, which claims priority to U.S. Provisional Patent Application 61/562,056 filed on Nov. 21, 2011, the contents of which are each hereby incorporated by reference in their entirety.

TECHNICAL FIELD

This disclosure is related to a respiratory assembly, and more particularly a respiratory assembly having a nostril engaging portion for providing sealable engagement with a treatment fluid.

BACKGROUND

Continuous positive air pressure (CPAP) masks are used for treating patients having any number of sleeping or breathing disorders during sleeping. The CPAP mask delivers a treatment fluid, such as ambient air or oxygen enriched air to a patient under a predetermined or desired pressure setting.

CPAP masks suffer from many disadvantages. For example, CPAP masks are bulky, making them less aesthetically and ergonomically pleasing. CPAP masks must provide sealable engagement with the patient's skin in order to maintain a sealed environment for achieving the desired pressure for treatment fluid delivery. This sealable engagement leaves wear marks on the patient's skin and may require undesirable amounts of time for the wear marks to disappear. Accordingly, many patients feel uncomfortable in public until the wear marks have disappeared, and male patients may not be able to shave their faces and female patients not be able to apply makeup until the wear marks have disappeared.

Due to the bulky nature of conventional CPAP masks, the masks occupy a large portion of a person's face. This restricts the person's ability to move their head during sleep because laying on the side of one's face may contact the CPAP mask and dislodge the mask from sealable engagement with the patient, thereby evacuating the pressure in the mask assembly. This is undesirable as either the patient is not receiving treatment gases under the ideal pressures or the patient is awakened.

Accordingly, there is a need for an improved CPAP mask or nasal assembly that addresses the disadvantages associated with conventional CPAP machines.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

According to at least one embodiment, a respiratory mask assembly is provided. The mask assembly includes a nasal engaging device having at least one post with a nasal engaging portion on about a first end thereof for delivering treatment gases to the nasal cavity of a patient. A mask is provided and has an inlet for receiving treatment gases from a fluid source and at least one receptacle for being sealably engaged with a respective one of the at least one post for delivering treatment gases from the inlet through the receptacle and into the nasal cavity of the patient.

According to at least one embodiment, a nasal assembly is provided. The nasal assembly includes a hose for allowing gaseous flowthrough. A pair of tubes is provided, each in gaseous communication with the hose. Further, a pair of posts, each post including a flange that defines an opening therein, the openings in gaseous communication with each corresponding tube of the pair of tubes. Each of the pair of tubes further includes an adhesive applied to each flange and configured for sealably engaging a patient's nare.

According to one or more embodiments, the nasal engaging portion includes a flange portion configured for engaging with a sheet having an adhesive applied thereon for being adhered and providing sealable engagement with the nostrils of the patient.

According to one or more embodiments, the adhesive is pressure sensitive.

According to one or more embodiments, the nasal assembly further includes a splitter engaged with the hose and each of the pair of tubes for allowing the gaseous flowthrough therebetween.

According to one or more embodiments, the splitter includes two splitter sockets for engaging each corresponding tube ball joint of the pair of tubes for allowing pivotal movement of the pair of tubes about the splitter.

According to one or more embodiments, the splitter includes two splitter ball joints for engaging each correspond tube socket of the pair of tubes for allowing pivotal movement of the pair of tubes about the splitter.

According to one or more embodiments, the pair of tubes are unitarily formed. According to some embodiments, the pair of tubes and the hose are unitarily formed.

According to one or more embodiments, the at least one post includes an extending portion on a second end thereof that is configured for selective engagement with the at least one receptacle or a corresponding tube of the pair of tubes.

According to one or more embodiments, the at least one post includes a connector on a second end thereof for connecting with the at least one receptacle or a corresponding tube of the pair of tubes.

According to one or more embodiments, each of the pair of posts or each of the pair of tubes or both include vent openings for allowing gaseous flowthrough. According to some embodiment, the vent openings are adjustable for titration of gases.

According to one or more embodiments, the inlet includes a swivel joint for allowing swiveling movement of the inlet about the mask.

According to one or more embodiments, the mask assembly or nasal assembly is configured for use with a continuous positive airway pressure (CPAP) machine.

According to one or more embodiments, the mask assembly or nasal assembly includes a hose for providing flowthrough of treatment gases from the fluid source to the inlet.

According to one or more embodiments, a CPAP mask is provided. The mask includes an inlet for receiving treatment gases from a fluid source, and at least one receptacle for being engaged with a post in sealable engagement with the nasal cavity of a patient and for delivering treatment gases from the inlet through the receptacle and into the nasal cavity of the patient.

According to one or more embodiments, the mask includes a pair of spaced-apart receptacles, each for engaging a respective post in sealable engagement with each nostril of the patient.

According to one or more embodiments, the nasal engaging device includes a seal in selective engagement with the adhesive.

According to one or more embodiments, the extending portion is a post ball joint and the receiving portion is a tube socket, and wherein the post ball joint and the tube socket are configured for selective engagement for allowing pivotal movement of the pair of tubes about each of the pair of posts.

According to one or more embodiments, the splitter includes two splitter sockets for engaging each corresponding tube ball joint of the pair of tubes for allowing pivotal movement of the pair of tubes about the splitter.

According to one or more embodiments, the splitter includes two splitter ball joints for engaging each correspond tube socket of the pair of tubes for allowing pivotal movement of the pair of tubes about the splitter.

BRIEF DESCRIPTION OF THE DRAWINGS

The foregoing summary, as well as the following detailed description of preferred embodiments, is better understood when read in conjunction with the appended drawings. For the purposes of illustration, there is shown in the drawings exemplary embodiments; however, the presently disclosed invention is not limited to the specific methods and instrumentalities disclosed. In the drawings.

DETAILED DESCRIPTION

The presently disclosed invention is described with specificity to meet statutory requirements. However, the description itself is not intended to limit the scope of this patent. Rather, the inventors have contemplated that the claimed invention might also be embodied in other ways, to include different steps or elements similar to the ones described in this document, in conjunction with other present or future technologies.

Figure 1:
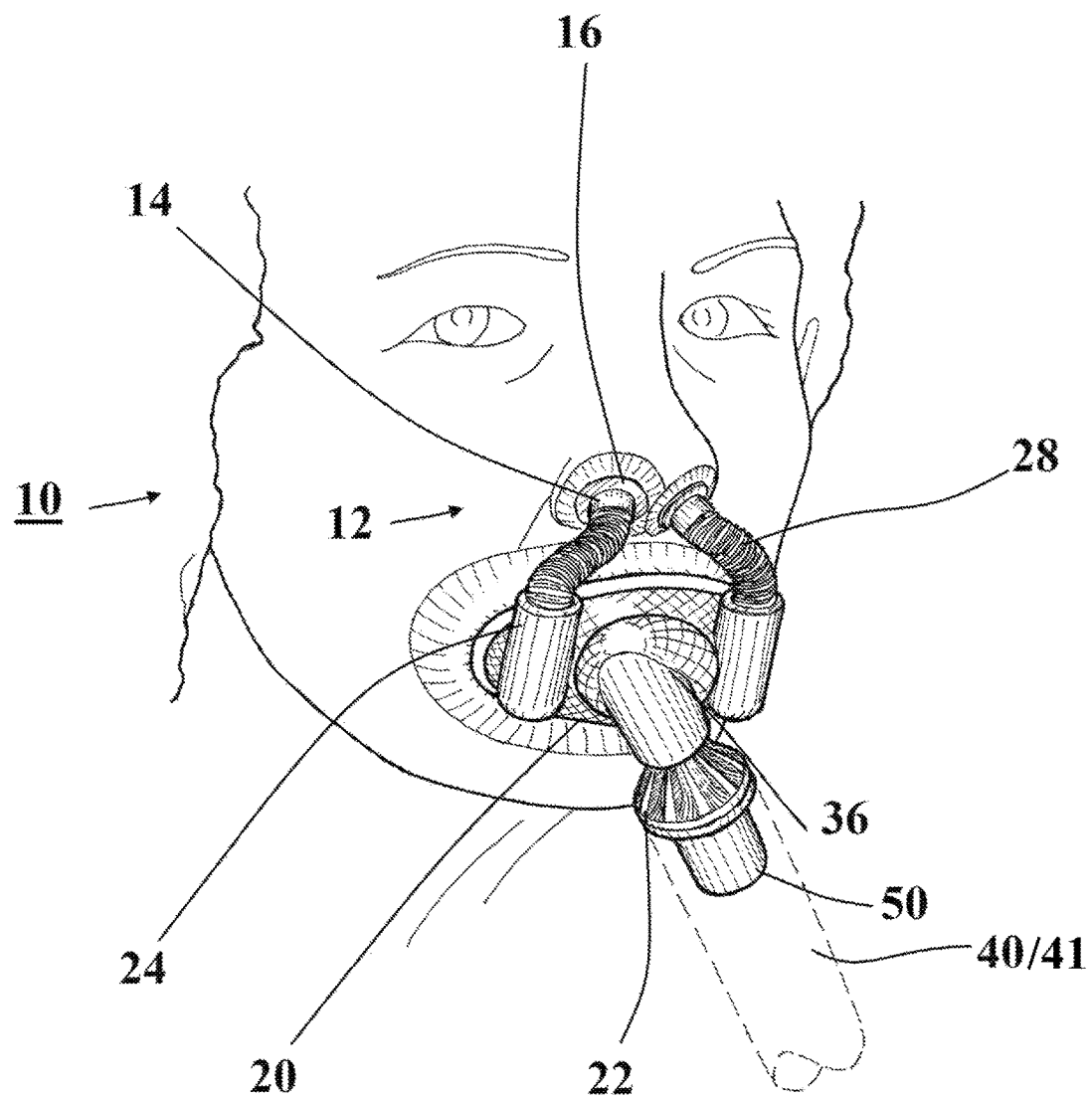
FIG. 1 illustrates a perspective view of a respiratory mask and a patient for being treated according to one or more embodiments disclosed herein.

FIG. 1 illustrates a respiratory mask assembly installed upon a patient 1 according to at least one embodiment. The mask assembly is generally designated as 10 throughout the drawings. The mask assembly 10 includes a nasal assembly 12. The nasal assembly may include at least one post 14 with a nasal engaging portion 16 on about a first end thereof for delivering treatment gases to the nasal cavity of the patient 1. The post 14 may be configured for providing a flush, sealable engagement with the patient's nares.

The mask assembly 10 may include a mask 20 having an inlet 22 for receiving treatment gases from a fluid source 41 and at least one receptacle 24 for being sealably engaged with the post 14. The fluid source 41 may be a continuous positive airway pressure (CPAP) machine, a fluid tank, a humidifier, or some other fluid source. The post 14 may be selectively engageable with the receptacle 24, such that the engagement is permanent or only when desired by the patient. Alternatively, the post 14 may be selectively engageable directly with a tube 28 carrying treatment gases therethrough.

Figure 2:
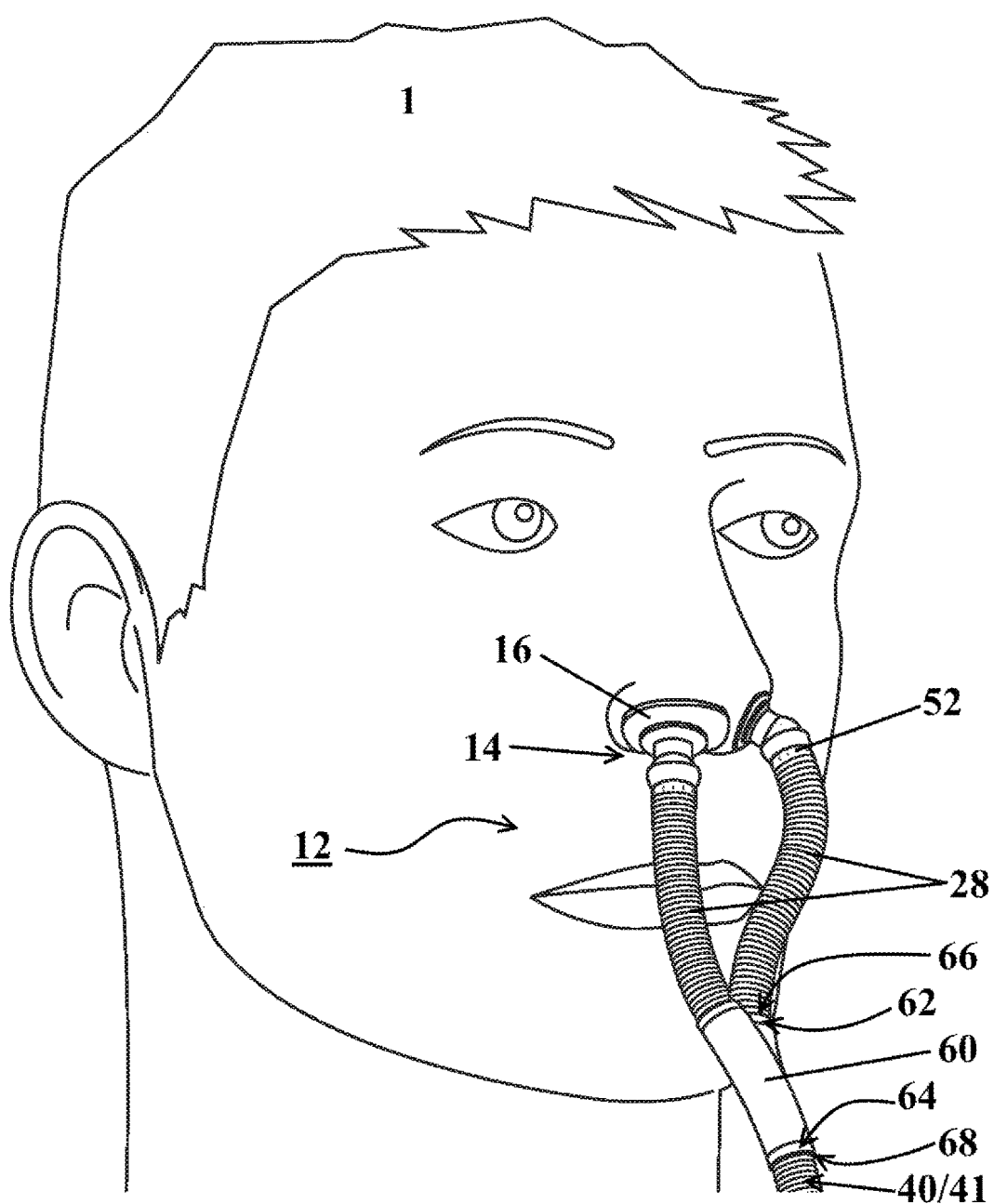
FIG. 2 illustrates a perspective view of a nasal assembly and a patient for being treated according to one or more embodiments disclosed herein.

FIG. 2 illustrates a nasal assembly 12 installed upon a patient 1 according to at least one embodiment. The nasal assembly 12 may include a pair of tubes 28, each in gaseous communication with a hose 40 or a fluid source 41. The pair of tubes 28 and the hose 40 may be unitarily formed. Alternatively a splitter 60 may be positioned between each of the pair of tubes 28 and the hose 40 or the fluid source 41. The splitter 60 may be engaged with each of the pair of tubes 28 and the hose 40 or fluid source 41 for allowing the gaseous flowthrough between each of the pair of tubes 28 and the hose 40 or the fluid source 41. The splitter 60, pair of tubes 28 and hose 40 may be unitarily formed.

The engagement of the splitter 60 with the tubes 28 and/or hose 40 or fluid source 41 may be achieved using a number of different structural configurations. Some structural configurations may permit greater pivotal movement between the elements 28, 40, 60, while at the same time maintaining a sealable engagement for preventing leakage of gas therefrom. The splitter 60 may have two tube-engaging ends 62 for engaging the tubes 28 and one source-engaging end 64 for engaging the hose 40 or fluid source 41. The tubes 28 may include a tube splitter receiver 66. The hose 40 or fluid source 41 may include a source splitter receiver 68. In some embodiments, the receivers 66, 68 or engaging ends 62, 64 may be circumferentially extending structures engaged with corresponding recess structures. Alternatively, the receivers 66, 68 or engaging ends 62, 64 may be splitter or tube sockets engaged with corresponding tube or splitter ball joints for allowing pivotal movement of the tubes 28 about the splitter 60.

Figure 3:
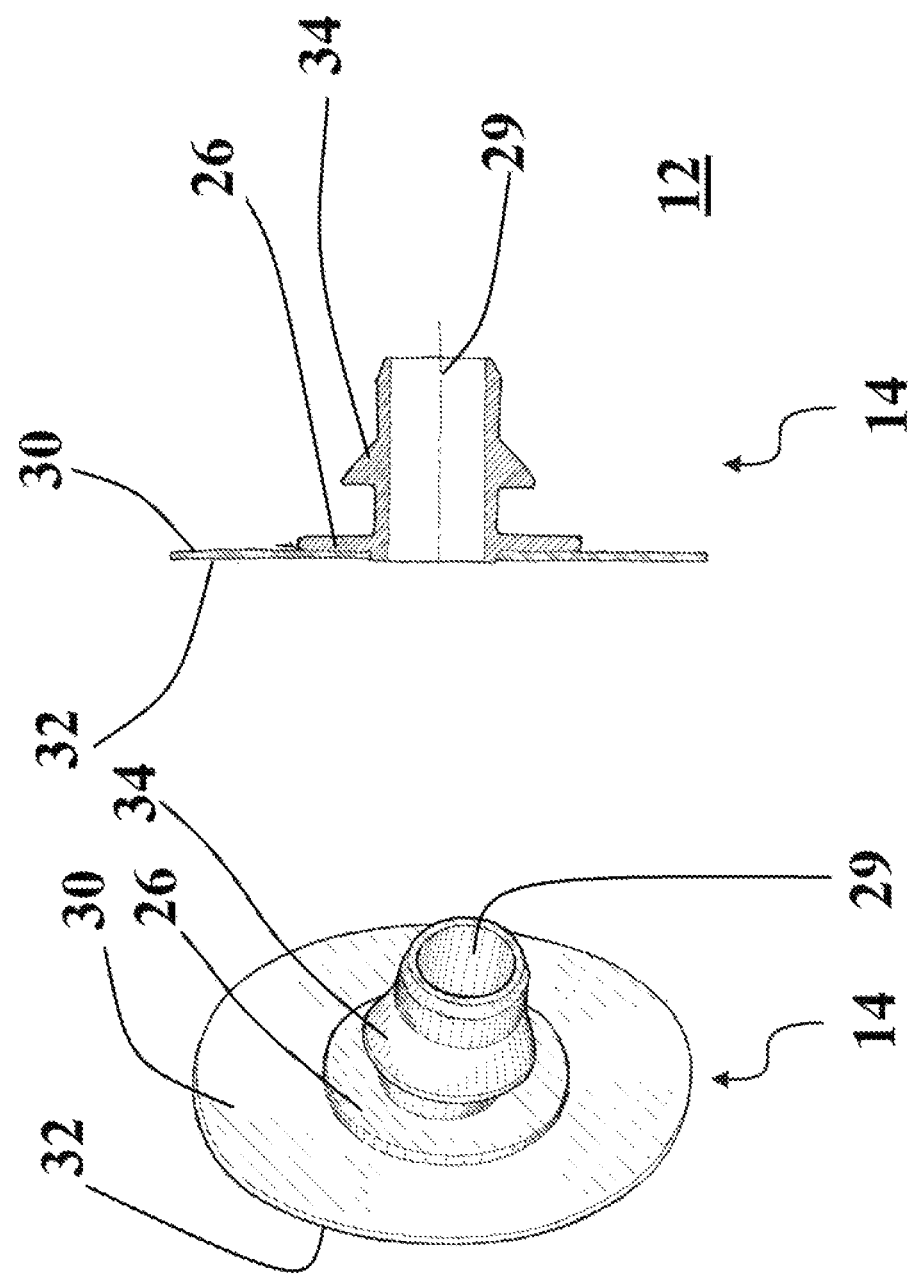
FIGS. 3A and 3B illustrate respective perspective and side views of a nasal assembly for use with a respiratory mask according to one or more embodiments disclosed herein.

According to some embodiments, the nasal assembly further includes a pair of posts 14. FIGS. 3A and 3B illustrate the nasal assembly 12 in greater detail according to at least one embodiment. The post 14 may include a flange 26 configured for engaging with a sheet 30 having an adhesive 32 applied thereon, or alternatively, a layer of adhesive 32, for being adhered and providing sealable engagement with the nostrils of the patient 1. The sheet 30 may have any desired shape, and may preferably include an opening therein for allowing flowthrough in an opening 29 defined in the post 14. The adhesive 32 may be a pressure sensitive adhesive such that the sheet 30 may be adhered and removed from the patient's nostrils as desired. The post 16 may include an extending portion 34 on a second end thereof that is configured for selective engagement with the at least one receptacle 24 or corresponding tube 28 of the pair of tubes 28.

In some embodiments, each post 14 of the pair of posts 14 may include a flange 26 that defines an opening 29 therein, the openings 29 in gaseous communication with each corresponding tube 28 of the pair of tubes 28. Further, an adhesive 32 or layer of adhesive 32 may be applied to each post 14, each post 14 configured for sealably engaging a patient's nare. The adhesive 32 may be applied to a sheet 30 positioned on a nasal facing side of the post 14, or the adhesive may be applied directly to the flange 26 of the post 14. The adhesive 32 may be pressure sensitive.

Figure 4:
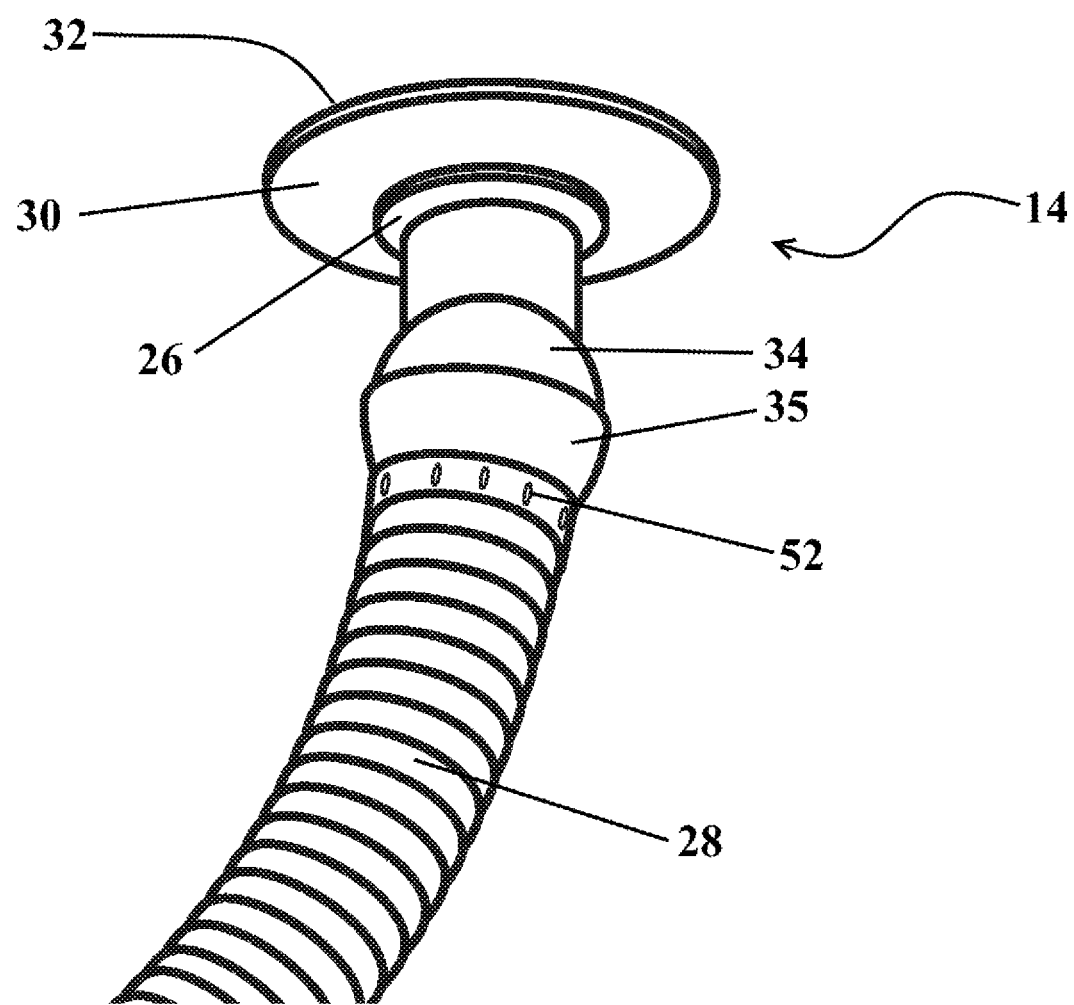
FIG. 4 illustrates a perspective view of a portion of a nasal assembly according to one or more embodiments disclosed herein.

In at least one embodiment, such as the embodiment depicted in FIG. 4, each post 14 of the pair of posts 14 may include an extending portion 34 for selectively engaging a respective receiving portion 35 of the pair of tubes 28. The engagement of the post 14 with the receptacle 24 or tube 28 may be achieved using a number of different structural configurations. The extending portion 34 may be a circumferentially extending portion for selectively engaging a respective recess receiving portion 35. Alternatively, the extending portion 34 may be a post ball joint and the receiving portion 35 being a tube socket, and wherein the post ball joint 34 and the tube socket 35 are configured for selective engagement for allowing pivotal movement of the pair of tubes 28 about each of the pair of posts 14, as depicted in FIG. 4. Another alternative embodiment may include the extending portion 34 being a post socket and the receiving portion 35 being a tube ball joint, wherein the post socket 34 and the tube ball joint 35 are configured for selective engagement for allowing pivotal movement of the pair of tubes 28 about each of the pair of posts 14.

In some embodiments, the nasal assembly 12 or mask assembly 10 may further include an oral device engagement 70 for engaging an oral device engaged with the patient's mouth. For example, but not limited to, the patient may have a mouth guard, mandibular advancement splint or some other oral device that may be used in conjunction with the nasal assembly 12 or mask assembly 10. The oral device engagement 70 may selectively engage the nasal assembly 12 or mask assembly 10 to the oral device for stabilizing the position of the nasal assembly 12 or mask assembly 10 with respect to the patient 1.

Figure 5:
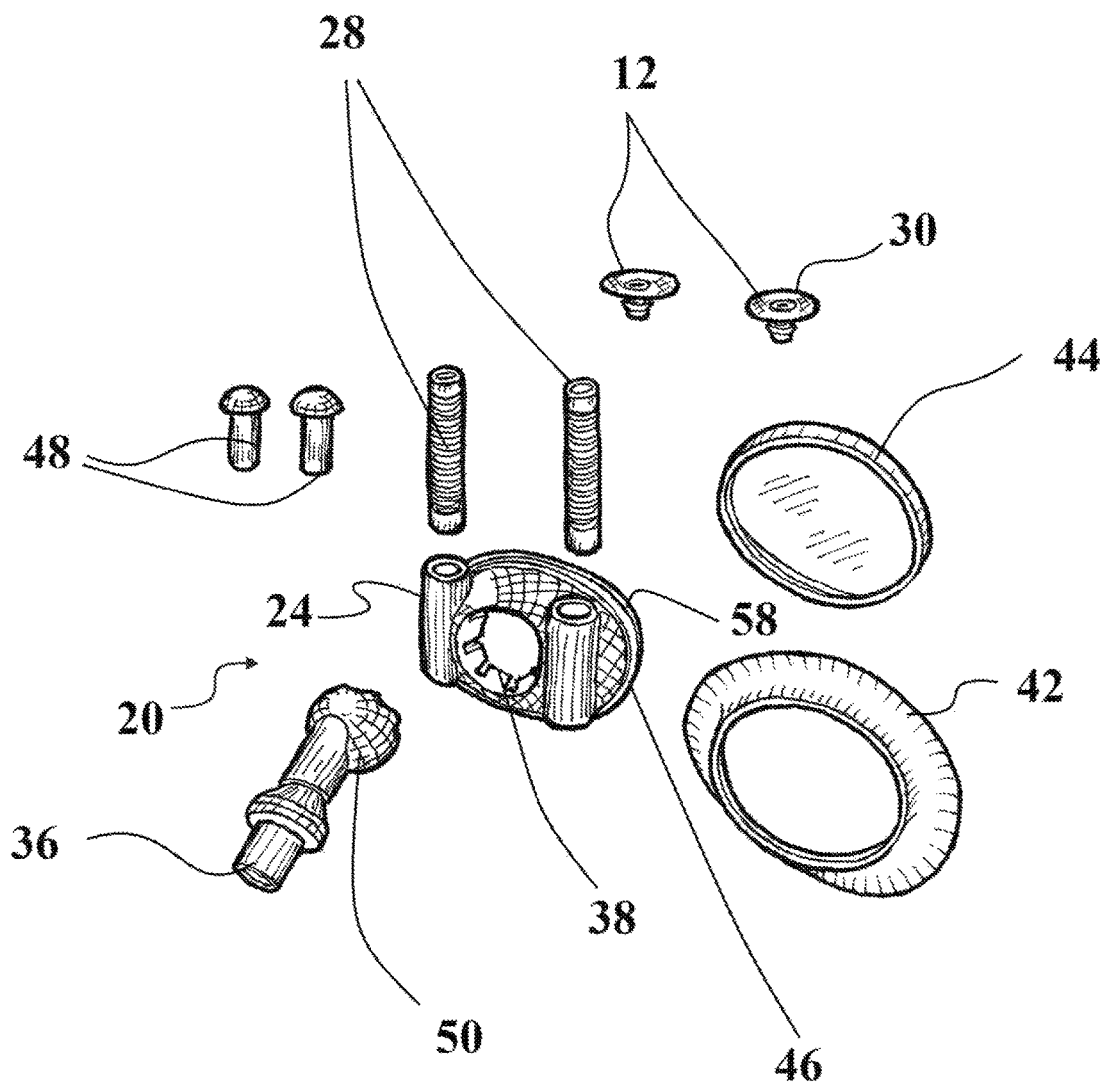
FIG. 5 illustrates a perspective view of a mask according to one or more embodiments disclosed herein.

As illustrated in FIG. 5, the inlet 22 may include a swivel joint 36 for allowing swiveling movement of the inlet 22 about the mask assembly 20. The inlet 22 may be a hose 40 for providing flowthrough of treatment gases from the fluid source 41 to the inlet 22.

The receptacle 24 may include a tube 28 configured for flexible movement to position the nasal assembly 12 to various sizes of respective patients' noses. As illustrated in more detail in FIG. 5, the mask 20 is configured for sealable engagement with the patient's mouth by an adhesive pad 42 selectively engageable therewith and carried by the mask body 46. Within the mask body 46 is defined a chamber 58 through which treatment gases flow from the inlet 22. In this manner, in one operative condition, the mask assembly 20 is sealably engaged with both the patient's mouth area while the nasal assembly 12 is also engaged with the patient's nares or nasal area. In this operative condition, treatment gases are being supplied to both the patient's mouth and their nasal area simultaneously. The mask body 46 may further define a socket recess 38 for cooperating with a joint described further herein.

Alternatively, panel 44 is provided for sealable engagement with the mask assembly 20 in order to seal off the chamber 58 so that treatment gases do not pass into the area surrounding the patient's mouth and instead pass only through to the nasal assembly 12. In this manner, the one or more devices 10 disclosed herein are appropriately configured for both CPAP applications in which the patient receives treatment gases to both their mouth and nose and in CPAP applications where the patient receives treatment gases to only their nose. Additionally, one or more plugs 48 may be provided for use with the mask 20 to seal receptacles 24 if the patient does not desire use of the nasal engaging configuration provided herein. Accordingly, the mask assembly 10 described herein has three distinct modes of operation: one in which treatment gases are being supplied to the patient's mouth only, one in which treatment gases are being supplied to the patient's nose only, and one in which treatment gases are being supplied to the patient's nose and mouth.

The patient may install a new adhesive pad 42 and sheet 30 after each use.

In one or more embodiments, the inlet may further include a ball and socket joint 50 as illustrated in FIG. 5, with ball being represented as 50 and socket recess being represented by 38. The ball and socket joint allows for rotational movement of the inlet 22. The ball 50 may define a plurality of vents 52 for allowing flow of treatment gases therethrough. The vents 52 may be adjustable in size and location such that manipulation of all exhaled fluids such as carbon dioxide from the patient is controlled and titratable such that the flow rate of fluids can be altered to a desired setting. In alternative embodiments, as depicted in FIGS. 2 and 4, each tube 28 of the pair of tubes 28, each post 14 of the pair of posts 14, or both may include vents or vent opening 52 for allowing gaseous flowthrough. Further, the vent openings 52 may be adjustable for titration of gases therethrough.

In one or more embodiments, the mask body 46 may include an adjustable mechanism that allows the tubing from the post 14 to be altered, moved or elevated to accommodate a patient's facial structure, primarily the distance between the nose and the oral housing port on or inside body 46, thereby allowing for ideal facial angles and facial length that might add to a patient's comfort. To further increase comfort, usability and effectiveness of the mask assembly 10 or nasal assembly 12, software and printing capabilities can be employed to customize the shape and contour of the various components mask assembly 10 and/or nasal assembly 12. For example, but not limited to, the nasal engaging portion 16 of the nasal assembly 12 may be specifically contoured to fit each nasal passage of the patient 1. Such customization can be achieved by digitally scanning the features of a patient's face to create a CAD model or for 3D printing. Further, various portions, or the whole of, the mask body 46 and/or adhesive pad 42 may be customized to more effectively fit the facial contours of the patient 1.

In one or more embodiments, the mask assembly may be provided as a short-term use product, such that the entire system is disposed of and replaced after a predetermined use period. For example, the mask assembly may be configured for use as a three month use product, such that the patient receives a new mask assembly every three months. Additionally, post 14 may be a disposable product.

While the embodiments have been described in connection with the preferred embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

The invention claimed is:

1. A maskless and strapless nasal assembly comprising:
a pair of posts, each post including:
a flange that defines an opening therein, the openings in gaseous communication with a hose or fluid source, the flange defining a mounting surface that defines a circumference;
an adhesive pad applied to each flange and configured for sealably engaging a patient's nare, wherein each adhesive pad defines an opening that is in fluid engagement with the opening of each flange, wherein the adhesive pad is planarly engaged with the mounting surface and extends radially outside of the entire circumference of the mounting surface, wherein the adhesive pad is defined at an end of each of the pair of posts such that each post does not extend into a respective nostril of the patient when the adhesive pad is engaged with the patient's nare;

a splitter engaged with each post of the pair of posts for allowing the gaseous communication with the hose or fluid source;

wherein each post is selectively and independently positionable relative to the other post to position a respective flange to engage with a respective nare of a patient, and wherein each of the posts are individually removable from the splitter for selective replacement thereof.

2. The nasal assembly of claim 1, wherein the adhesive is pressure sensitive.

3. The nasal assembly of claim 1, wherein the splitter includes two splitter sockets for engaging each of the pair of posts for allowing pivotal movement of the pair of posts about the splitter.

4. The nasal assembly of claim 3, wherein the splitter sockets are balls or sockets of ball and socket joints.

5. The nasal assembly of claim 3, wherein the splitter further includes a hose socket for engaging the hose or fluid source for allowing pivotal movement of the hose or fluid source about the splitter.

6. The nasal assembly of claim 5, wherein the hose socket is a ball or a socket of a ball and socket joint.

7. The nasal assembly of claim 1, wherein the pair of posts and the hose are selectively engageable.

8. The nasal assembly of claim 1, wherein each of the pair of posts include vent openings for allowing gaseous flowthrough.

9. The nasal assembly of claim 1, wherein the splitter includes vent openings for allowing gaseous flowthrough.

10. The nasal assembly of claim 1, wherein the post is customized to fit a shape of the patient's nare.

11. The nasal assembly of claim 1, wherein the adhesive is applied at a terminal end of each flange, and wherein the adhesive is in direct contact with a patient's nare.

12. A nasal assembly comprising:
a hose for allowing gaseous flowthrough;
a splitter engaged with the hose and each of a pair of posts for allowing gaseous flowthrough therebetween;
the pair of posts, each post including:
a flange that defines an opening therein, the openings in gaseous communication with the splitter, the flange defining a mounting surface that defines a circumference;
a pressure sensitive adhesive pad applied to each flange and configured for sealably engaging a patient's nare, wherein each adhesive pad defines an opening that is in fluid engagement with the opening of each flange, wherein the adhesive pad is planarly engaged with the mounting surface and extends radially outside of the entire circumference of the mounting surface, wherein the adhesive pad is defined at each of an end of the pair of posts such that each post does not extend into a respective nostril of the patient when the adhesive pad is engaged with the patient's nare,
wherein each of the pair of posts includes an extending portion for selectively engaging a respective receiving portion of the splitter, wherein each post is selectively and independently positionable relative to the other post to position a respective flange to engage with a respective nare of a patient, and wherein each of the posts are individually removable from the splitter for selective replacement thereof.

13. The nasal assembly of claim 12, wherein the adhesive is applied at a terminal end of each flange, and wherein the adhesive is in direct contact with a patient's nare.

14. A nasal assembly comprising:
a hose for allowing gaseous flowthrough;
a splitter engaged with the hose and each of a pair of posts for allowing the gaseous flowthrough therebetween;
each post of the pair of posts including:
a flange that defines an opening therein, the openings in gaseous communication with the splitter, the flange defining a mounting surface that defines a circumference;
a pressure sensitive adhesive pad applied to each flange and configured for sealably engaging a patient's nare, wherein each adhesive pad defines an opening that is in fluid engagement with the opening of each flange, wherein the adhesive pad is planarly engaged with the mounting surface and extends radially outside of the entire circumference of the mountain surface, wherein the adhesive pad is defined at each of an end of the pair of posts such that each post does not extend into a respective nostril of the patient when the adhesive pad is engaged with the patient's nare,
wherein each of the pair of posts includes a post ball joint for selectively engaging a splitter socket, and wherein each of the pair of posts include vent openings for allowing gaseous flowthrough;
wherein each post is selectively and independently positionable relative to the other post to position a respective flange to engage with a respective nare of a patient, and
wherein each of the posts are individually removable from the splitter for selective replacement thereof.

15. The nasal assembly of claim 14, wherein the splitter includes two splitter sockets for engaging each corresponding post ball joint of the post for allowing pivotal movement of the posts about the splitter.

16. The nasal assembly of claim 14, wherein the splitter includes a hose ball joint for engaging a hose socket for allowing pivotal movement of the hose about the splitter.

17. The nasal assembly of claim 14, wherein the adhesive is applied at a terminal end of each flange, and wherein the adhesive is in direct contact with a patient's nare.

18. A nasal assembly comprising:
a hose for allowing gaseous flowthrough;
a splitter engaged with the hose and each of a pair of posts for allowing gaseous flowthrough therebetween;
the pair of posts, each post including:
a flange that defines an opening therein, the openings in gaseous communication with the splitter, the flange defining a mounting surface that defines a circumference;
a pressure sensitive adhesive pad applied to each flange and configured for sealably engaging a patient's nare, wherein each adhesive pad defines an opening that is in fluid engagement with the opening of each flange, wherein the adhesive pad is planarly engaged with the mounting surface and extends radially outside of the entire circumference of the mounting surface, wherein the adhesive pad is defined at each of an end of the pair of posts such that each post does not extend into a respective nostril of the patient when the adhesive pad is engaged with the patient's nare, wherein each of the pair of posts includes an extending portion for selectively engaging a respective receiving portion of the splitter, wherein each post is selectively and independently positionable relative to the other post to position a respective flange to engage with a respective nare of a patient, and wherein each of the posts are individually removable from the splitter for selective replacement thereof.

19. The nasal assembly of claim 18, wherein each of the pair of posts include vent openings for allowing gaseous flowthrough.

20. The nasal assembly of claim 19, wherein the vent openings are adjustable for titration of gases.

21. The nasal assembly of claim 18, wherein the extending portion is a post ball joint and the receiving portion is a splitter socket, wherein each of the pair of posts include vent openings for allowing gaseous flowthrough.

\* \* \* \* \*